United States Patent [19]
Righter et al.

[11] Patent Number: 5,581,369
[45] Date of Patent: Dec. 3, 1996

[54] APPARATUS AND METHOD FOR COMMUNICATING ELECTROCARDIOGRAPHIC DATA TO A FACSIMILE MACHINE

[75] Inventors: William H. Righter, Aloha; Andrew J. Nicoll, Hillsboro; Jeff Gilbert, Portland, all of Oreg.

[73] Assignee: Ralin, Inc., Bannockburn, Ill.

[21] Appl. No.: 951,212

[22] Filed: Sep. 25, 1992

[51] Int. Cl.⁶ .................................................. A61B 5/04
[52] U.S. Cl. .......................................... 358/442; 128/904
[58] Field of Search .......................... 358/482; 128/702, 128/711, 706, 696330323

[56] References Cited

U.S. PATENT DOCUMENTS

| | | | |
|---|---|---|---|
| 3,733,033 | 11/1973 | Rodbard | 128/2.06 |
| 3,819,863 | 6/1974 | Slaght . | |
| 3,872,252 | 3/1975 | Malchman et al. . | |
| 3,938,507 | 2/1976 | Sarnoff et al. . | |
| 4,055,729 | 10/1977 | Vandling . | |
| 4,120,294 | 10/1978 | Wolfe . | |
| 4,221,223 | 9/1980 | Linden . | |
| 4,337,377 | 6/1982 | Van Riper et al. . | |
| 4,531,527 | 7/1985 | Reinhold, Jr. et al. . | |
| 4,535,783 | 8/1985 | Marangoni . | |
| 4,606,352 | 8/1986 | Geddes et al. . | |
| 4,622,979 | 11/1986 | Katchis et al. . | |
| 4,802,008 | 1/1989 | Walling . | |
| 4,843,478 | 6/1989 | Nowell . | |
| 4,858,617 | 8/1989 | Sanders . | |
| 4,862,896 | 9/1989 | Reinhold, Jr. et al. . | |
| 4,889,134 | 12/1989 | Greenwold et al. . | |
| 4,938,228 | 7/1990 | Righter et al. . | |
| 4,974,607 | 12/1990 | Miwa . | |
| 4,991,200 | 2/1991 | Lin . | |
| 5,029,590 | 7/1991 | Allain et al. . | |
| 5,041,918 | 8/1991 | Ishida et al. . | |
| 5,050,612 | 9/1991 | Matsumura . | |
| 5,226,431 | 7/1993 | Bible et al. | 128/908 |

OTHER PUBLICATIONS

Portfolio Companies "Oregon Resource & Technology Development Corporation," Copyright 1990, cover page through p. 2 and p. 19.

Tompkins, Willis J., "Patient Worn, Intelligent Arrhythmia Systems," *IEEE Engineering In Medicine and Biology Magazine*, Dec. 1985.

*Primary Examiner*—Bernard Roskoski
*Attorney, Agent, or Firm*—Leydig, Voit & Mayer, Ltd.

[57] ABSTRACT

An apparatus and method for receiving digitized electrocardiographic (ECG) data, converting that data into a form suitable for reception by a facsimile device, and transmitting the data over a standard telephone line to a remote facsimile device. The apparatus includes an encased unit having modular connectors facilitating ready hookup to a telephone, a wall-type phone jack, a power source and a recording unit. The unit remains interconnected between the telephone and phone line, but is transparent to the operator and outside callers during normal telephone use. To facilitate easy use by the operator, a remote programmability feature is provided so that various user parameters stored in the apparatus may be accessed and reprogrammed from a remote touch-tone telephone.

19 Claims, 12 Drawing Sheets

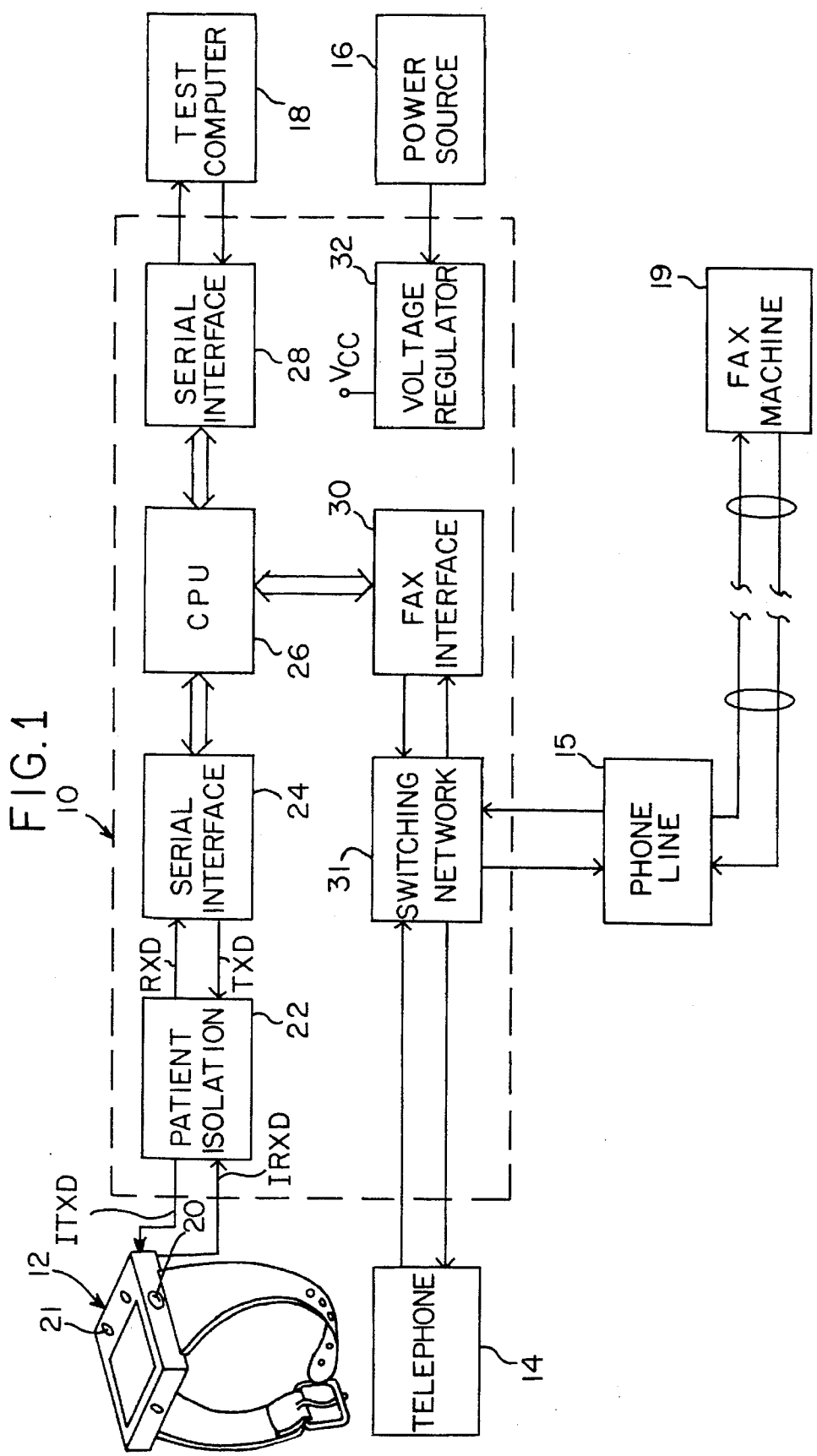

| Setting | a0 | a1 | a2 | a3 | a4 | a5 | a6 | a7 | a8 | a9 | a10 | a11 | a12 | a13 | a14 |
|---|---|---|---|---|---|---|---|---|---|---|---|---|---|---|---|
| no_filter | 256 | 0 | 0 | 0 | 0 | 0 | 0 | 0 | 0 | 0 | 0 | 0 | 0 | 0 | 0 |
| 16 Hz | 66 | 58 | 39 | 17 | -1 | -10 | -10 | -4 | 1 | 3 | 3 | 1 | 0 | -1 | -1 |
| 18 Hz | 74 | 64 | 38 | 10 | -8 | -13 | -7 | 0 | 5 | 4 | 1 | -1 | -1 | -1 | 0 |
| 20 Hz | 82 | 68 | 36 | 3 | -14 | -12 | -2 | 5 | 5 | 2 | -2 | -2 | -1 | 0 | 1 |
| 22 Hz | 90 | 72 | 32 | -4 | -17 | -9 | 3 | 7 | 3 | -2 | -3 | -1 | 1 | 1 | 0 |
| 24 Hz | 99 | 76 | 26 | -12 | -18 | -3 | 8 | 6 | -1 | -4 | -1 | 1 | 1 | 0 | -1 |
| 28 Hz | 114 | 80 | 13 | -22 | -11 | 9 | 8 | -3 | -5 | 0 | 3 | 0 | -1 | -1 | 1 |
| 32 Hz | 129 | 80 | -3 | -25 | 3 | 13 | -2 | -7 | 2 | 4 | -1 | -2 | 1 | 1 | 0 |
| 36 Hz | 148 | 79 | -18 | -19 | 14 | 5 | -10 | 1 | 5 | -2 | -2 | 2 | 0 | -1 | 0 |
| 40 Hz | 164 | 73 | -30 | -6 | 17 | -8 | -5 | 7 | -2 | -3 | 3 | 0 | -1 | 1 | 0 |

FIG. 9B

APPARATUS AND METHOD FOR COMMUNICATING ELECTROCARDIOGRAPHIC DATA TO A FACSIMILE MACHINE

FIELD OF THE INVENTION

The present invention relates to an apparatus and method for communicating electrocardiographic (ECG) data to a remote facsimile machine, and more particularly, to an apparatus and method for converting ECG data into a bit-image graphic representation and communicating it to a remote facsimile machine.

BACKGROUND OF THE INVENTION

Episodic cardiac symptoms, such as arrhythmia, are triggered by a wide variety of events including stress. In order for physicians to effectively diagnose the cause of the attack, they must analyze the particular pattern of the heartbeat irregularity. Electrocardiographic data is commonly used in such an analysis. Unfortunately, most arrhythmias are spontaneous and unpredictable, making detection nearly impossible while at the physician's office.

Portable electrocardiogram monitoring and recording devices for use by persons in outpatient environments have long been known. These devices include those which can be conveniently clipped on to a user's belt for wear throughout his daily routine. With the unit constantly in place, the user can simply press a button to signal the onset of an arrhythmia attack, whereby the unit begins recording the user's ECG data.

Typically, this type of portable unit is equipped with a sufficient amount of internal memory to record several minutes of ECG data. The unit can then be taken into the physician's office where inspection can be made of the electrocardiogram pattern recorded during the arrhythmia episode. Recent ECG recording devices have been equipped with modem interfaces to relieve the user of the burden of traveling to the physician's office. Instead, the modem interface permits the ECG data to be transmitted to the physician's office over a standard telephone line.

While these devices have provided for the effective capture and transmission of ECG data from outpatient environments to a physician's office, further improvements and efficiencies can be achieved. A shortcoming in having a modem transfer the ECG data to the physician's office is that a computer or a transtelephonic receiver must be dedicated at the physician's office to monitor the receiving modem for incoming transmissions. This imposes a significant cost on the office, as computer systems or transtelephonic receivers typically cost several thousand dollars. With a dedicated computer, there is the additional inconvenience that the physician is required to examine the data while on the computer or that someone in the physician's office is required to attend the computer and direct the incoming ECG data to a printer for later inspection by the physician.

In recent years, low-cost facsimile machines have been incorporated into virtually all business offices. Since most physicians' offices are presently equipped with facsimile machines, transmission of ECG data directly to such a machine would provide a substantial cost savings by eliminating the need for a dedicated computer. Furthermore, facsimile devices automatically provide a print-out that the physician may inspect at his convenience. It is, therefore, desired to have a portable device that can receive ECG data from a recorder, convert this data into facsimile format, and transmit the data over a standard phone line to a remote facsimile machine.

SUMMARY OF THE INVENTION

In view of the foregoing, it is a primary object of the present invention to provide an apparatus and method for receiving ECG data and converting this data to facsimile format for transmission over standard telephone lines to a remote facsimile machine.

A related object of the present invention is to provide a portable apparatus having modular connections for easy installation between a telephone and phone line.

Another object of the present invention is to provide an apparatus that can remain interconnected between a telephone and phone line, without interfering with normal telephone operation.

Still another object of the present invention is to provide an apparatus that can be programmed from a remote location by a person using a touch-tone telephone.

A further object of the present invention is to provide an apparatus that can be connected to an external computer to simplify testing during manufacture and to promote software development.

The present invention includes a portable apparatus having electronic circuitry primarily comprising a receiving section, a processing section, and a transmitting section. The receiving section is adapted to receive digitized ECG data from a compatible recording unit and store the data in sequential memory locations. The processing section filters unwanted bioelectric signals from the received data and then performs a bit-image generation, whereby the data is transformed into a format suitable for graphic display. Next, the processing section compresses the image data to convert it into a format suitable for transmission to a facsimile machine. Finally, the transmitting section takes the processed data and converts it into a format suitable for transmission over a standard telephone line.

The electronic circuitry of the present invention is enclosed in a portable housing having modular connectors that facilitate installation of the apparatus. Specifically, the installation procedure is accomplished by interconnecting a standard telephone cable between an output connector of the apparatus and a wall jack, and connecting a second telephone cable between an input connector on the apparatus and a telephone. Installation is completed by connecting the apparatus to a power source. No external settings or adjustments are required by the user. When the user wants to transmit ECG data, a third cable is connected between the apparatus and the recording device. This allows ECG data stored in the recording device to be transferred to the apparatus. Alternatively, the ECG data can be transferred telemetrically or by some other suitable wireless medium.

At all times other than during transmission of ECG data, the apparatus is transparent to normal telephone use, even though it remains interconnected between the telephone and the wall jack.

Consistent with the user-friendly design of the present invention is the further aspect of remote programmability. The apparatus of the present invention is adapted to detect various combinations of touch tone frequencies, or DTMF codes, to signal a change in certain pre-programmed information. The information that can be programmed includes, but is not limited to, the bandwidth of the input filter, the patient's identification number (the patient ID), the patient's phone number, the phone number of the selected remote facsimile machine, and a feature to disable call waiting during ECG data transmission.

Other objects and advantages of the present invention will become apparent from the following description when taken in conjunction with the drawings, in which:

BRIEF DESCRIPTION OF THE DRAWINGS

FIG. 1 is a block diagram of the entire system, showing the control unit in dashed line and all peripheral devices connected therewith;

FIG. 9B is a table showing the coefficients for the gain elements of FIG. 9A for achieving various filter band widths; and FIG. 10 is representative of how ECG data is arranged and displayed on a facsimile printout following processing and transmission by the present invention.

DETAILED DESCRIPTION

Figure 2A:
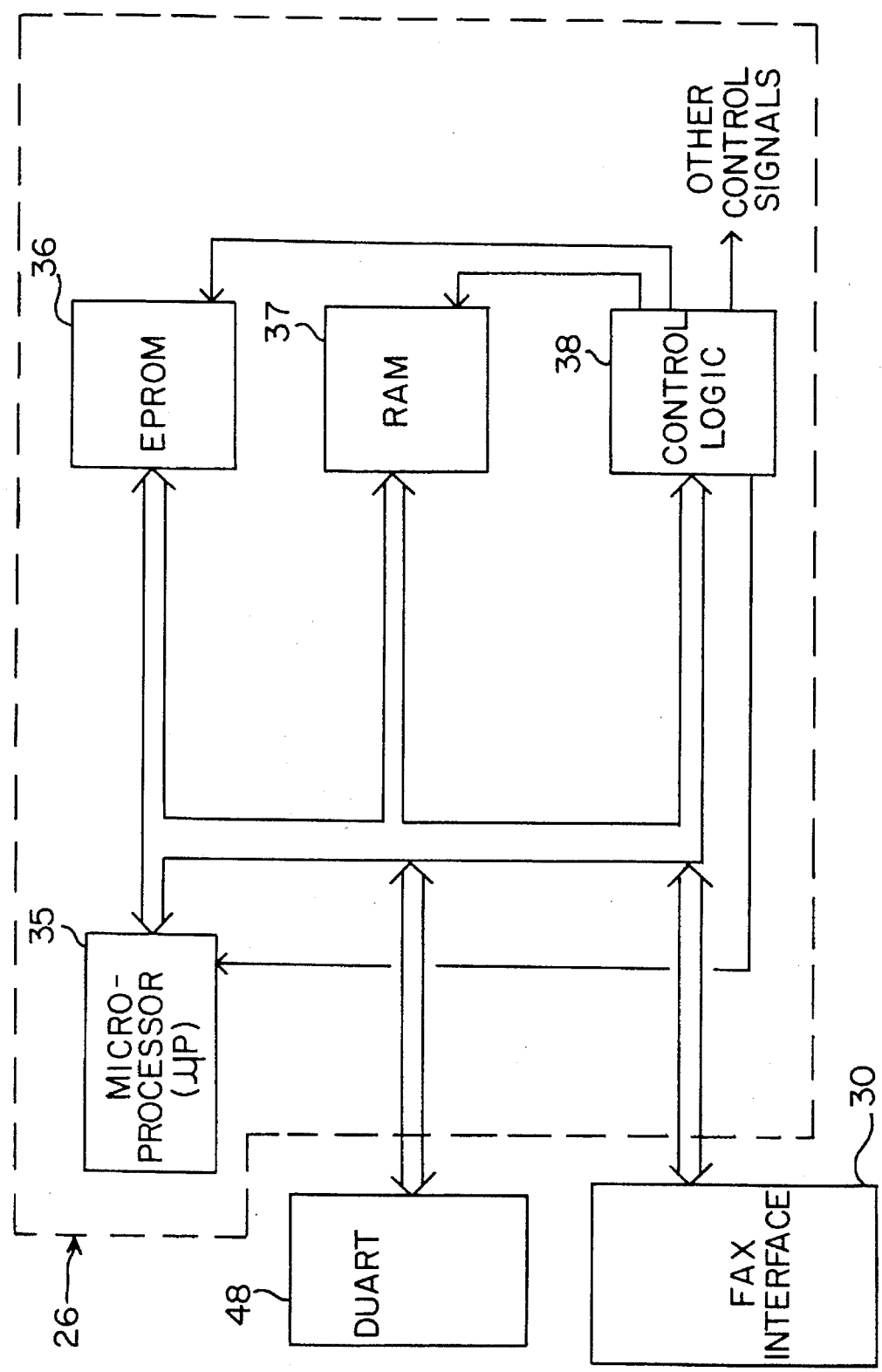
FIG. 2A shows a physical block diagram of the CPU including the microprocessor, the control logic, and volatile and nonvolatile memories.
Figure 2B:
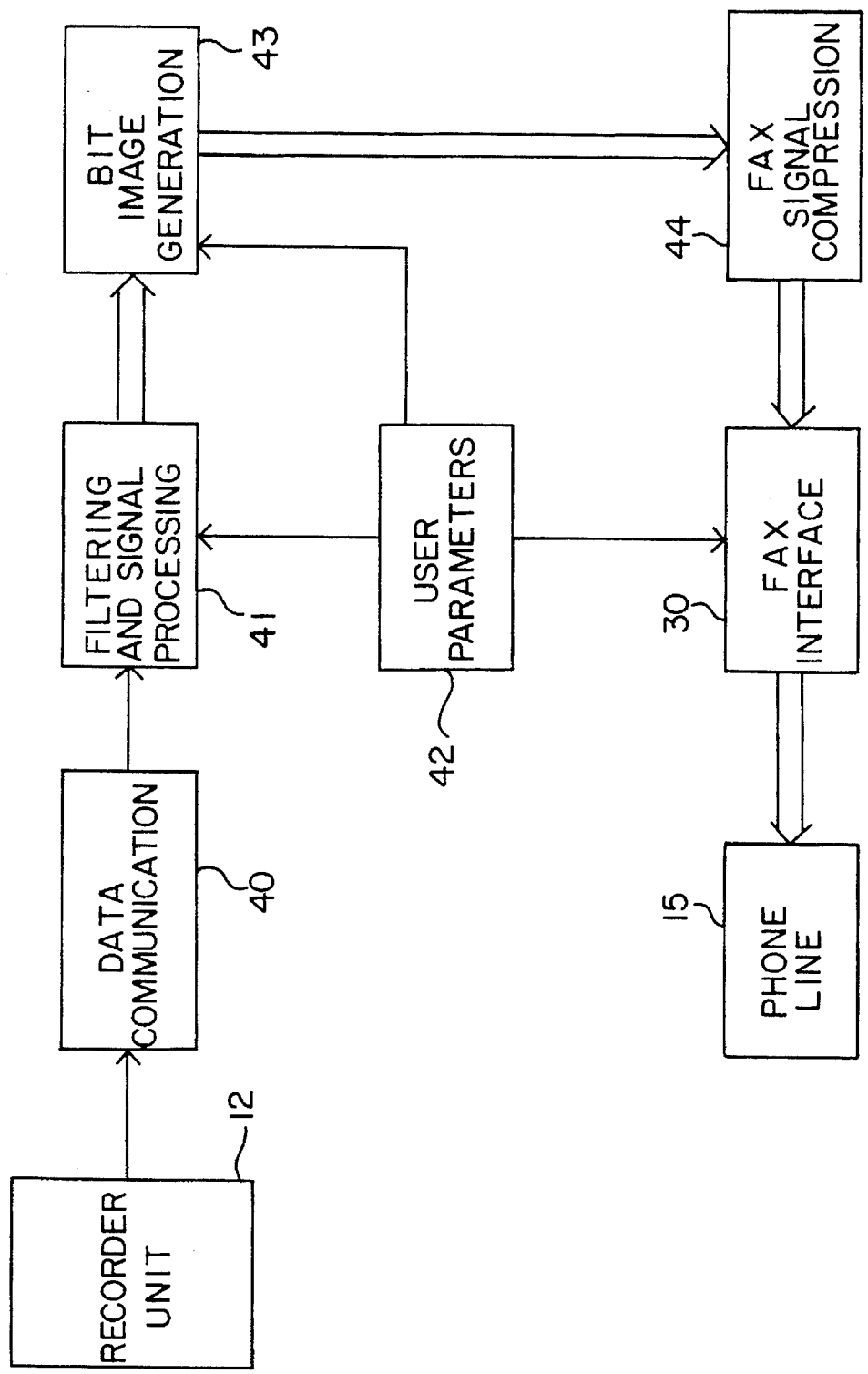
FIG. 2B is functional block diagram depicting the data flow as it passes from the recorder unit through the control unit, where it is processed, and finally out to the phone line.
Figure 3:
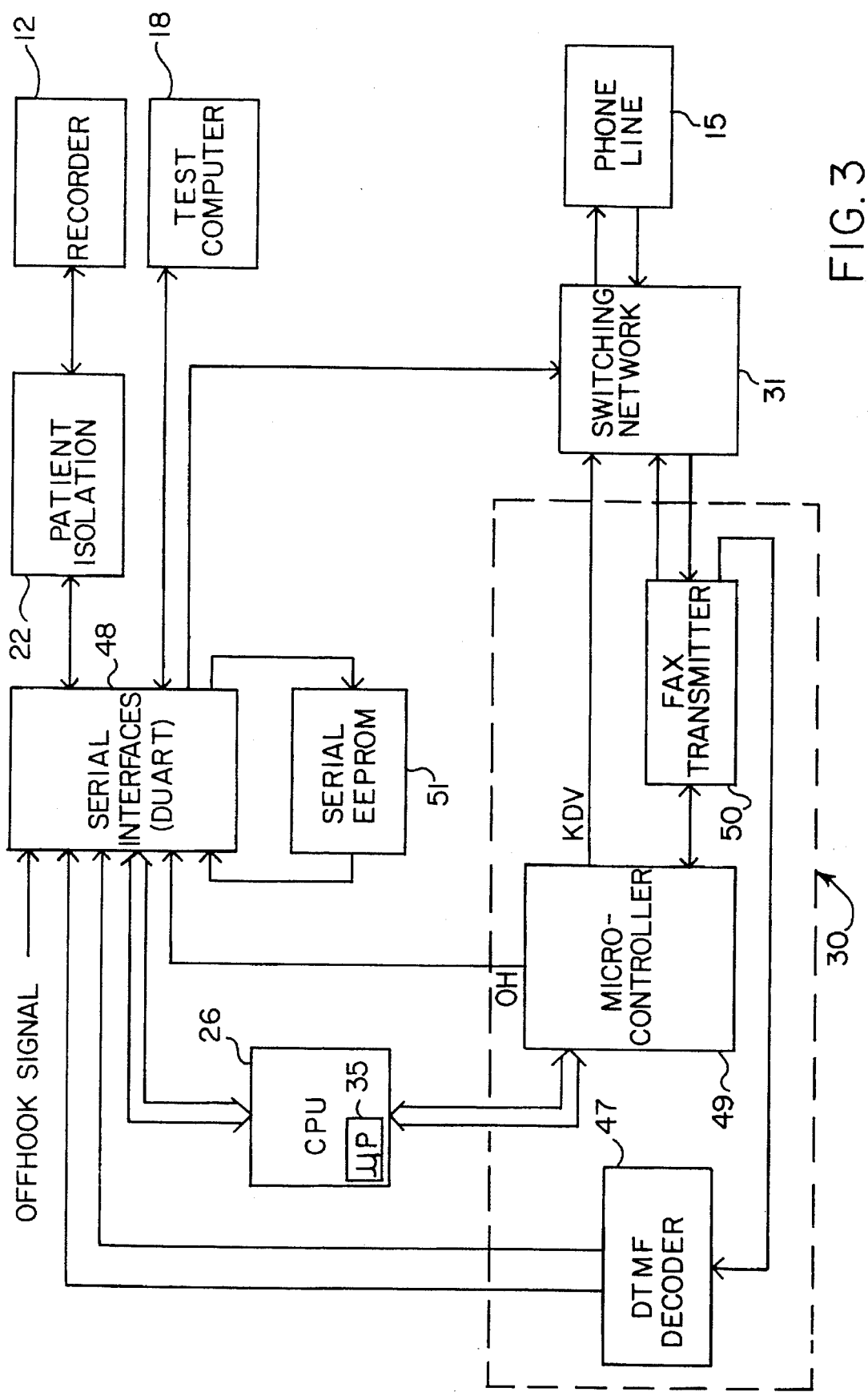
FIG. 3 is a block diagram, partially overlapping with that of FIG. 1, showing the facsimile interface and serial interfaces in more detail.
Figure 4:
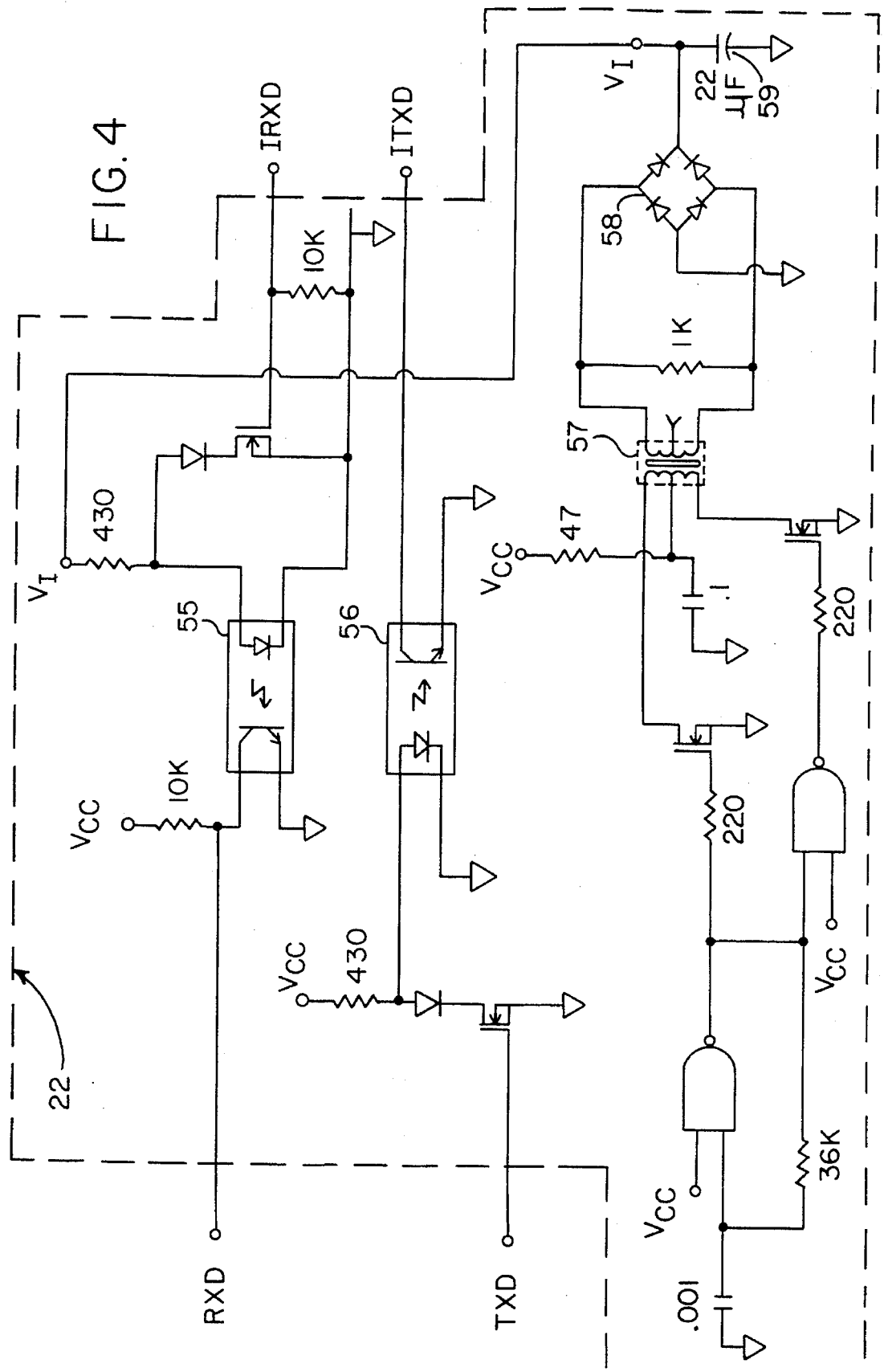
FIG. 4 is a schematic diagram of the isolation circuitry utilized by the present invention.
Figure 5:
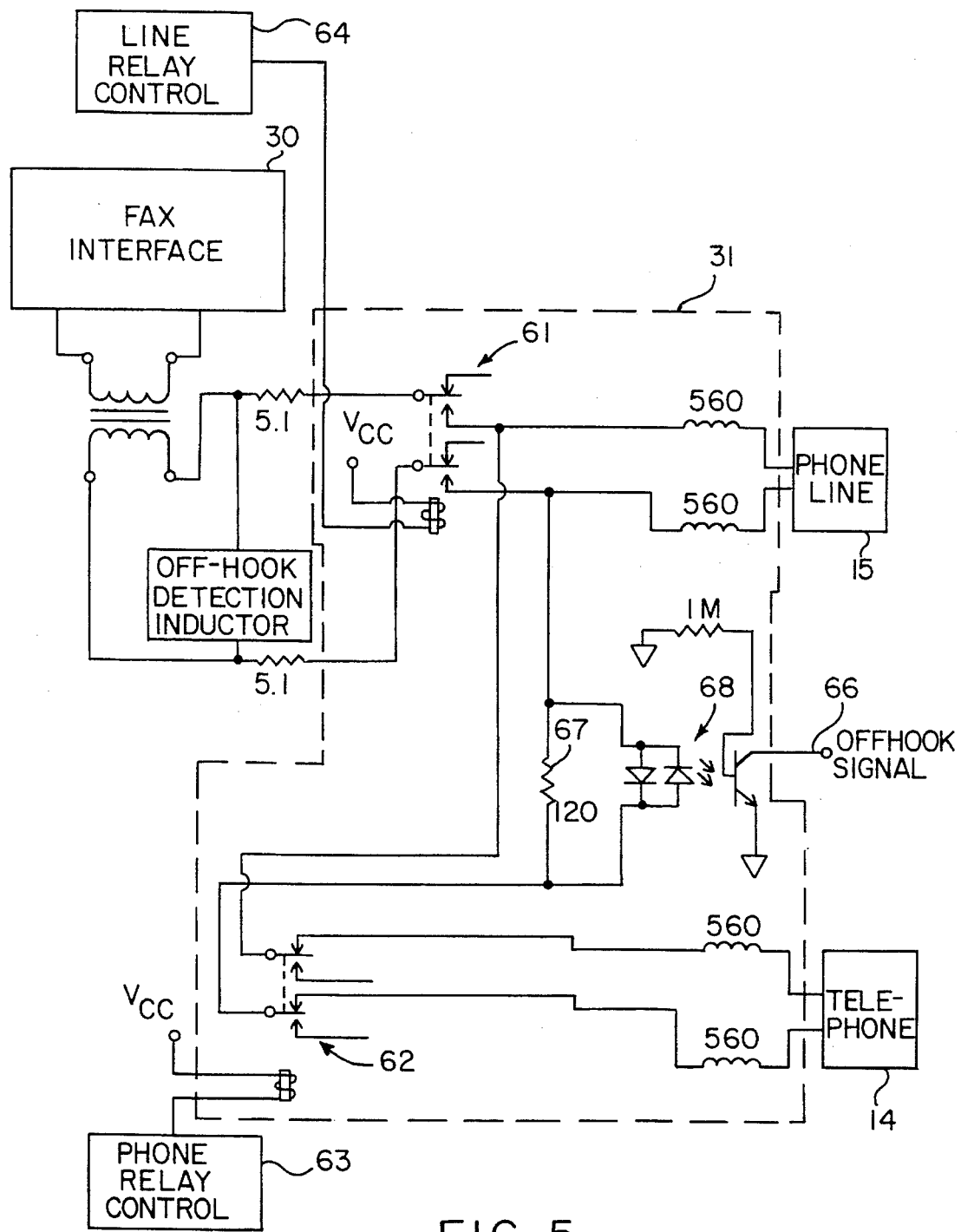
FIG. 5 is a schematic diagram of the switching network circuitry used in the present invention.

Turning now to the drawings, FIGS. 1 through 5 collectively depict the architecture and electrical interconnections of the present invention. FIGS. 1, 2, and 3 are block diagram representations of the hardware configuration. Commonly known and available commercial components are selected to effectuate the functionality of each of these functional blocks. Detailed circuit schematics have generally not been provided, as the block diagram representations are sufficient to enable persons of ordinary skill in the art to make and use the present invention. FIGS. 4 and 5, however, show schematic level diagrams for two of the functional blocks shown in FIGS. 1 and 3 which are unique to the present invention. These include isolation circuitry and a switching network, and will be discussed in more detail below.

Referring first to FIG. 1, a control unit generally designated by the reference numeral 10 is provided for connection to a compatible recording unit 12, a telephone 14, a phone line 15, a power source 16, and a test computer 18. The recording unit 12 is configured so as to provide a serial stream of digitized ECG data to the control unit 10. In its broadest aspect, the control unit 10 converts this data into a bit-image format for graphic display, and transmits it over a phone line 15 to a remote facsimile machine 19.

Preferably, although not necessarily, the recording unit 12 is a wrist-worn unit of the type disclosed in U.S. Pat. No. 5,191,891, assigned to the assignee of the present invention, which is incorporated herein by reference. This recorder 12 is adapted to be worn on the wrist of a user, whereby the user can conveniently signal the onset of an arrhythmia attack by contacting one or more conductive electrodes 20 (only one of which is shown in FIG. 1). Contacting the electrodes 20 initiates a routine for capturing medical grade ECG data, which is digitized and stored in internal memory. Typically, the memory size is sufficient to store several minutes of ECG data. The data remains in this internal memory until some later time when the user couples the recording unit 12 to the control unit 10 and initiates the transmission of ECG data therebetween by depressing a transmit button 21 on the recording unit. The recording unit and the control unit are preferably designed for physical (i.e., wired) coupling, but it will be readily appreciated that they may be designed for some other form of electrical coupling (such as telemetric or infrared).

The recorder 12 transmits the digitized ECG data to the control unit 10 in a serial format. Isolation circuitry 22, as will be described in more detail below, buffers the electrical connection between the recording unit 12 and a serial interface 24 in the control unit. A primary feature of the isolation circuitry 22 is that it isolates the voltage levels between the control unit circuitry and the recorder circuitry. This prevents inadvertent electrical shock by isolating the user from the higher voltages of the wall outlet and phone line, which are connected to the control unit 10. An inherent feature of this isolation is to inhibit the intercommunication of electrical noise signals and ground loops between the two units.

Data output from the isolation circuitry 22 is directed to the input of a serial interface 24. This interface 24 accepts the serialized data and converts it into proper parallel form so that it may be readily accessible by the central processing unit (CPU) 26. A second serial interface 28 performs a similar conversion function and is provided for communication with a test computer 18, as discussed below. The CPU 26, in addition to providing the centralized synchronization and control for the control unit 10, executes software program routines to convert the ECG data into a format suitable for recognition by a standard facsimile machine 19.

A facsimile interface 30 is adapted for connection between the CPU 26 and phone line 15, and provides appropriate data conversion therebetween. In the forward-going direction, facsimile image data generated by the CPU 26 is directed to the facsimile interface 30. This data is then converted and formatted into a form suitable for transmission over a standard telephone line. In the reverse direction, information transmitted across the telephone line 15 is received into the facsimile interface 30 and converted into an appropriate digital form that can be directly read by the CPU 26. In certain embodiments, the control unit 10 may be configured only for the transmission of facsimile image data, with information transmitted in the reverse direction limited to handshaking and other protocol signals.

A switching network 31 provides selective electrical interconnections among the facsimile interface 30, the telephone line 15 and a telephone 14. Responsive to control signals generated by the CPU 26, the switching network 31 automatically provides the appropriate electrical interconnections. During normal telephone use, for example, the switching network 31 directly connects the telephone 14 with the phone line 15, whereby the presence of the control unit 10 is transparent. During facsimile transmissions, however, the switching network 31 interconnects the facsimile interface 30 with the telephone line 15, while disconnecting the telephone 14. Once the facsimile transmission is complete, the CPU 26 automatically reconnects the phone line 15 with the telephone 14.

In a preferred embodiment, the control unit 10 employs modular connectors (not shown in the figures) to facilitate simple installation of the control unit 10 with the recorder 12, telephone 14, phone line 15, and power source 16. There is also an internal connector to support an external computer 18, which can be used for purposes such as testing and debugging during manufacture or later servicing. As previously mentioned, the control unit 10 is transparent to normal telephone operation. Thus, a one-time installation procedure facilities quick and convenient use by the user. It can be readily appreciated that the cable interconnecting the recorder 12 and the control unit 10 is the only connection the user need make for a given transmission.

Also not shown in the figures are user controls and status indicators provided on the control unit 10. More particularly, the control unit 10 includes several LEDs that function as visual indicators and provide status information to the user. These include ready/receive, transmit, and error indicators. The ready/receive indicator, for example, operates as a power indicator by remaining illuminated when the control unit is on and indicates that data is being received by turning off during data transmissions between the recorder 12 and the control unit 10. Upon completion of a data transmission (i.e., when the buffer memory is full), the ready/receive indicator blinks to signal to the user that the transmission is complete and the control unit 10 is ready to transmit the facsimile image over the telephone line. In a similar fashion, the transmit indicator illuminates while data is being transmitted between the control unit 10 and the phone line 15. The error indicator provides notice to the user that an error event has been encountered, thereby signalling the user to take appropriate, corrective action.

In a preferred embodiment, only two user controls are provided on the control unit 10. These include a power switch which, when on, completes an electrical signal path at the power input to apply power to the control unit. As will be discussed in more detail later, internal relays are configured so as to electrically connect the telephone to the phone line when the power is off, thereby making the presence of the control unit 10 transparent to normal telephone operation. Also, a push button ("SEND") switch is provided on the control unit 10 to initiate the data transmission between the control unit 10 and phone line 15.

Other functional blocks shown in FIG. 1 relate to the power supply and voltage regulation for the present invention. In a preferred embodiment, the input voltage to the control unit 10 optimally ranges between 7.2 and 12 volts DC. A voltage regulation circuit 32 utilizes a series regulator to convert this input voltage into a regulated 5 volt output. The power source 16 can be any of a number of commercially-available transformer units that plug directly into a wall outlet converting the 120 volt, 60 cycle AC into a DC value between 7.2 and 12 volts. It will be further appreciated that, consistent with the design of the present invention, a conventional transformer and rectifier circuit could be included within the control unit 10, whereby the control unit 10 could be directly powered by the voltage from a wall outlet.

Referring next to FIG. 2A, a physical block diagram of the CPU 26 is shown which is comprised primarily of a microprocessor 35, erasable programmable read-only memory (EPROM) 36, random-access memory (RAM) 37 and control logic 38. In a preferred embodiment, a 68000 series microprocessor available from Motorola is used. The 68000 is a low-cost, 16-bit microprocessor which effectively performs the processing operations required in the present invention. Software or program code (i.e., a set of machine coded instructions) for execution by the microprocessor 35 is stored in the non-volatile memory space of the EPROM 36. The RAM 37, or volatile memory, provides the storage area for the downloaded ECG data, the facsimile bit-image data, and other temporary storage values. Preferably, the control logic 38 is comprised primarily of two programmable array logic (PAL) devices which generate the necessary control signals for synchronizing operations with the microprocessor 35. Specifically, 22V10 series PAL devices, which are produced by a variety of manufactures and commonly known in the art, are employed in a preferred embodiment.

The electrical interconnections between the microprocessor 35, EPROM 36, RAM 37, and control logic 38 are commonly known and understood in the art and are not, therefore, described in detail. Similarly, the microcode and logic equations describing the operation of the PAL devices are not shown and described, as a person of ordinary skill in the art would commonly understand how to effectuate the necessary control signals of the present invention.

FIG. 2B is a functional block diagram showing the data flow through the control unit 10. A data communication section 40 receives the digitized data transmitted from the recorder unit 12 in a serial format. It then converts the data from serial to parallel form and stores it in RAM 37, where it can be accessed by the microprocessor 35. Next, a signal processing routine 41 filters the data to remove noise and other undesired bioelectric signal components. In a preferred embodiment, the filtering is performed by the CPU utilizing a finite impulse response (FIR) low pass filtering routine as the data is being received. As will be later discussed, any of a variety of filter bandwidths can be selected for optimizing performance. Data specifying the particular bandwidth selected is stored in non-volatile memory, along with a variety of other user parameters 42.

After the filtering routine is complete, a bit-image generation 43 is performed so as to produce a graphical representation of the ECG data. It will be appreciated by persons skilled in the art that, during this image generation procedure, a quadratic interpolation is performed, whereby the interpolation generates a functional value that is resampled at a data rate corresponding to the facsimile bit rate. As in the filtering routine 41, user parameters 42 are input to facilitate the image generation 43. Particularly, information such as the patient ID and the selected bandwidth are integrated into the generated image for ultimate display by the facsimile machine—either on a generated facsimile cover sheet or on the printout of the ECG data. FIG. 10 illustrates a typical display of ECG data as it is ultimately output by the facsimile machine.

Next, an image compression routine 44 reduces the image data into a standardized format for transmission to a remote facsimile machine 19. The compressed data is then input into the facsimile interface 30 where it is converted from a digital value to a voltage level and format suitable for transmission over the telephone line 15. The data format and protocol generated by the present invention for transmissions to facsimile machines are governed by international standards. Specifically, the International Telegraph and Telephone Consultative Committee (CCITT) has published specifications describing such standards. Publications CCITT T.4 and CCITT T.30 respectively provide the telephone system standards for generating bit-images and the transmission protocol for facsimile machines.

Referring next to FIG. 3, further detail is provided concerning the serial interfaces 24, 28 and the facsimile interface 30 of FIGS. 1 and 2A. A dual asynchronous receiver/transmitter (DUART) 48 provides the two independent serial interface sections 24,28. The DUART 48 transforms serial data received from either the recorder 12 or the test computer 18 into parallel form. As each byte is received, the DUART 48 generates an interrupt, signalling to the microprocessor 35 in the CPU 26 that a data byte has been received. The microprocessor 35 processes this interrupt by reading the data byte from the DUART 48 and storing it in memory, or taking other appropriate action.

The facsimile interface 30 (shown in broken line in FIG. 3) is comprised primarily of three chips: a dual-tone multi-frequency (DTMF) decoder 47; a micro-controller 49; and a modem/facsimile transmitter 50. In a preferred embodiment, a companion chip set (part numbers SC11075 and SC11054) manufactured by Sierra Semiconductor is used as the micro-controller 49 and the modem/facsimile transmitter 50.

The CPU 26 communicates directly with the micro-controller 49, such that data may be read from or written to the micro-controller 49 directly to or from the microprocessor 35. The collective operation of the chip set 49,50 is to accept digital data from the microprocessor 35 and convert it into a form suitable for direct coupling to a standard phone line 15. Conversely, the chip set 49,50 accepts data transmissions from the phone line 15 and converts it into a digital form, which may be read by the microprocessor 35.

In accordance with an important aspect of the present invention, the control unit 10 is designed to receive and interpret programming information supplied from a remote touch-tone telephone. As is commonly known, telephone keypad buttons generate a tone comprised of two separate frequencies (i.e., a DTMF signal). DTMF signals generated by a remote telephone are transmitted over the phone line and received by the modem/facsimile transmitter chip 50, which directs them to the DTMF decoder 47.

The DTMF decoder 47 translates the two frequency components (i.e., the tone pairs) of the signals into a numerical value between 0 and 15. Several bits in the parallel port on the DUART 48 are used to read the numerical value, such that it can be utilized by the microprocessor 35. In this way, the software determines which remote telephone keypad buttons were depressed and thereby effectuates the tone programming routine.

Also shown in FIG. 3 is a serial electrically erasable programmable read-only memory (EEPROM) 51. This EEPROM 51 is interfaced for access by the DUART 48 and provides the non-volatile storage area for various programmable user parameters (such as the patient ID, the phone number for the destination facsimile machine, and the filter bandwidth). Various control codes are encoded in the patient ID and can be used, for example, to disable the call waiting feature while a facsimile image is being transmitted.

FIG. 4 shows the isolation circuitry that buffers the interconnection between the recording unit 12 and serial interface 24. This circuitry is primarily effectuated through a pair of opto-couplers 55 and 56, and an isolation transformer 57. With specific reference to the isolation transformer circuitry, standard electronic components including two NAND gates, a resistor, and a capacitor are connected in a feedback configuration so as to generate an unstable, or oscillating signal. In a preferred embodiment, the resistor and capacitor values are selected so as to effectuate an oscillatory or AC signal of approximately 20 kilohertz, which is applied to the primary winding of the transformer 57. The transformer output, taken off the secondary winding, is passed through a rectifier 58 and a filter capacitor 59. This isolation supply voltage, designated as $V_I$, is used to power the side of the opto-couplers 55, 56 that is electrically connected with the recording unit 12. In this way, the respective supply voltages of the control unit 10 and the recorder unit 12 are effectively isolated, thereby eliminating any potential shock hazard to the user wearing the wrist recorder 12. It also, advantageously, eliminates ground loops and the exchange of noise signals between the control unit 10 and recorder 12.

FIG. 5 is a detailed schematic of the switching network 31 of FIG. 1. The network is primarily comprised of a line relay 61 and phone relay 62. A phone relay control 63 selectively connects and disconnects the telephone 14 from operable connection with the phone line 15. In a similar fashion, a line relay control 64 effectively connects and disconnects the telephone 14 and phone line 15 from the facsimile interface 30.

In a preferred embodiment, these relay control signals are generated by the micro-controller 49 and the DUART 48 (FIG. 3). Specifically, the "OH" (Off Hook) signal line of the SC11075 micro-controller 49 is input to the DUART 48, where it is monitored by software control. An output line from the DUART 48, also under software control, provides the actuating signal for the phone relay 62. The actuating signal for the line relay 61 is provided directly by the "KDV" (Data/Voice Control) output line of the micro-controller 49.

FIG. 5 also shows the circuitry used for generating an "OFF HOOK" detection signal on line 66. Taking the receiver of the telephone 14 off hook causes current to flow through a resistor 67. This, in turn, activates an opto-coupler 68, causing the "OFF HOOK" signal line 66 to change state. This signal is fed into the input port of the DUART 48 (see FIG. 3), where it is read by the microprocessor 35 for use in the software routines.

Figure 6:
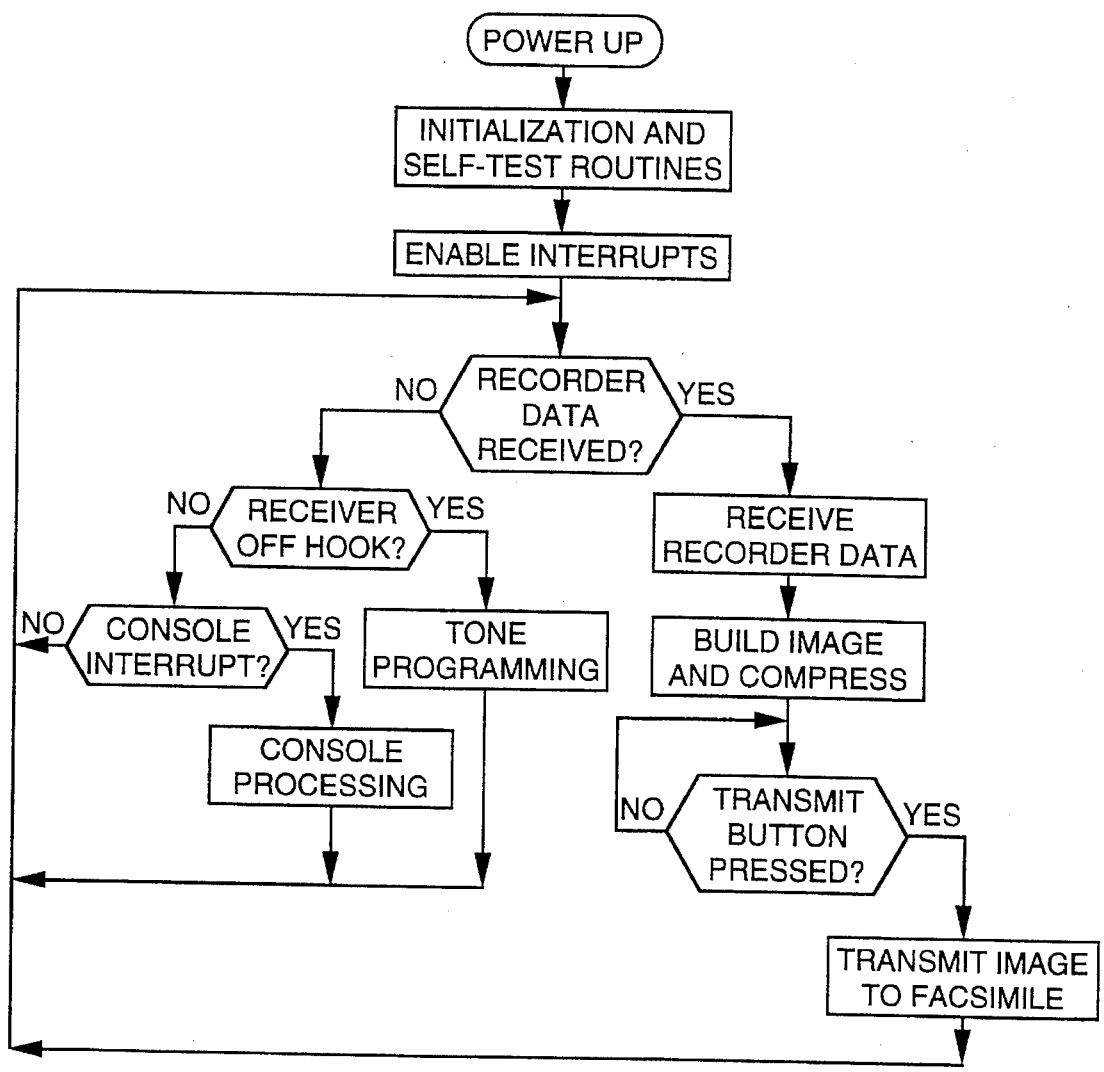
FIG. 6 is a flowchart showing the top level software operation of the present invention.
Figure 7:
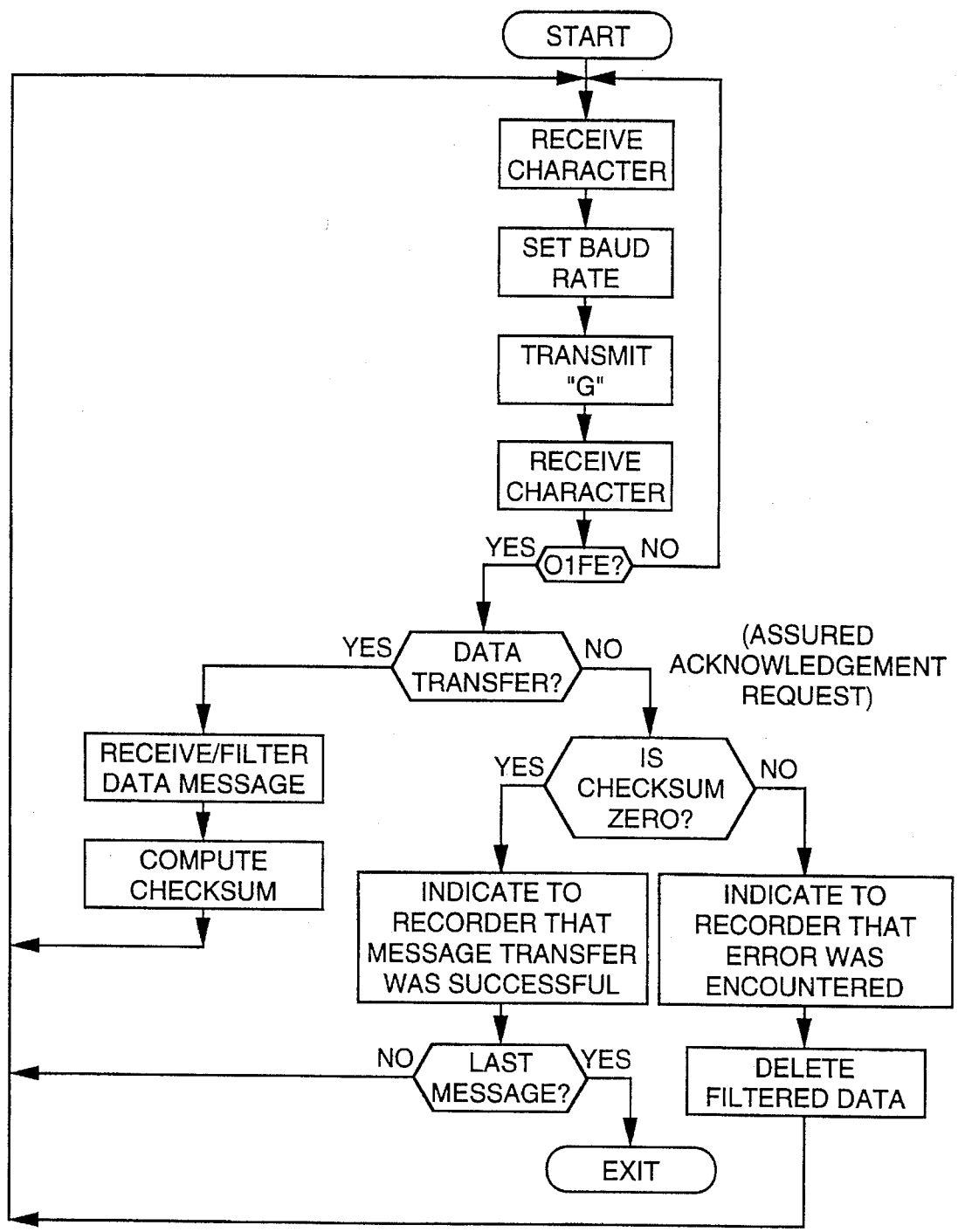
FIG. 7 is a flowchart depicting the data receiving routine utilized by the software of the present invention.
Figure 8A:
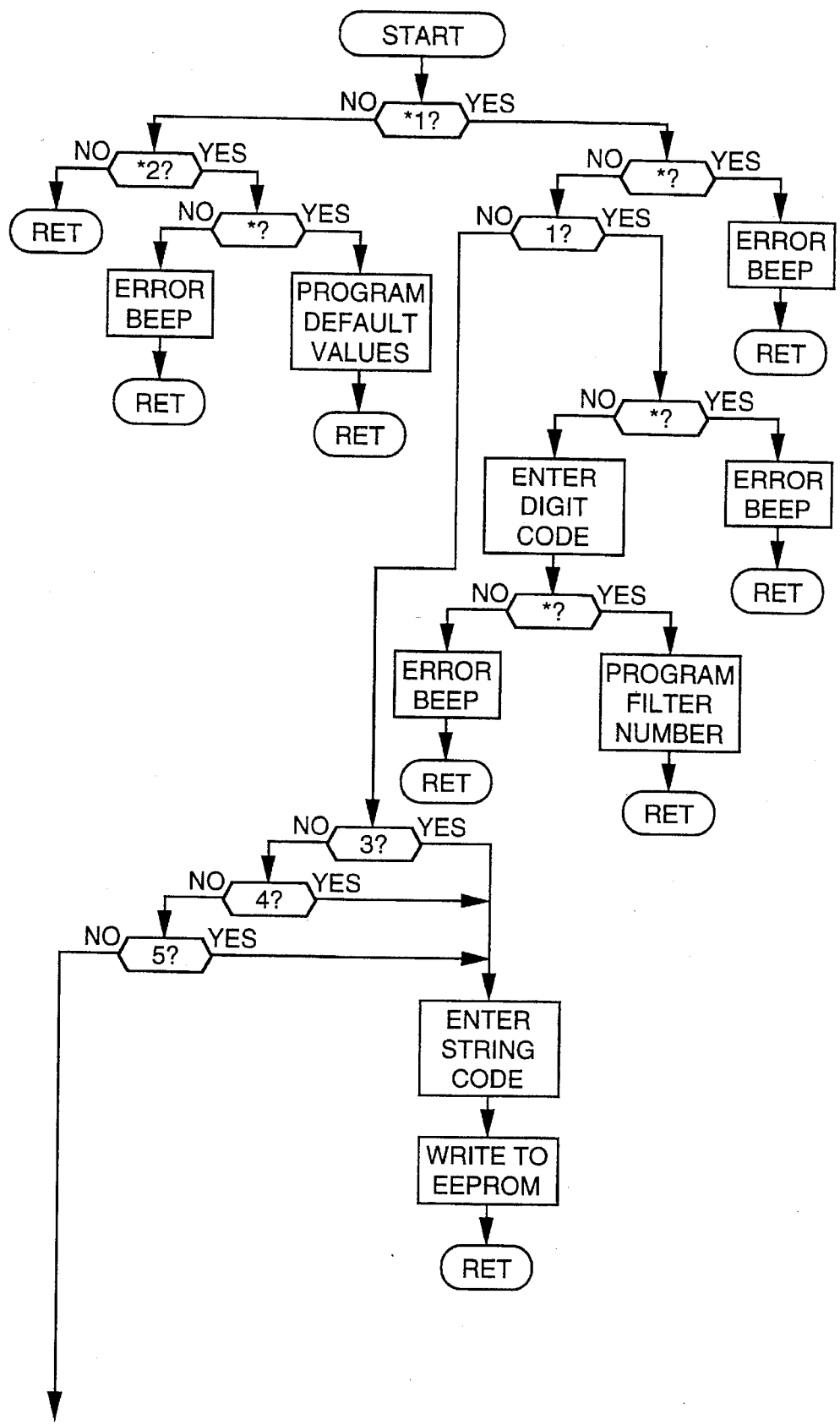
FIG. 8 is a flowchart illustrating the operation of the tone programming routine.
Figure 8B:
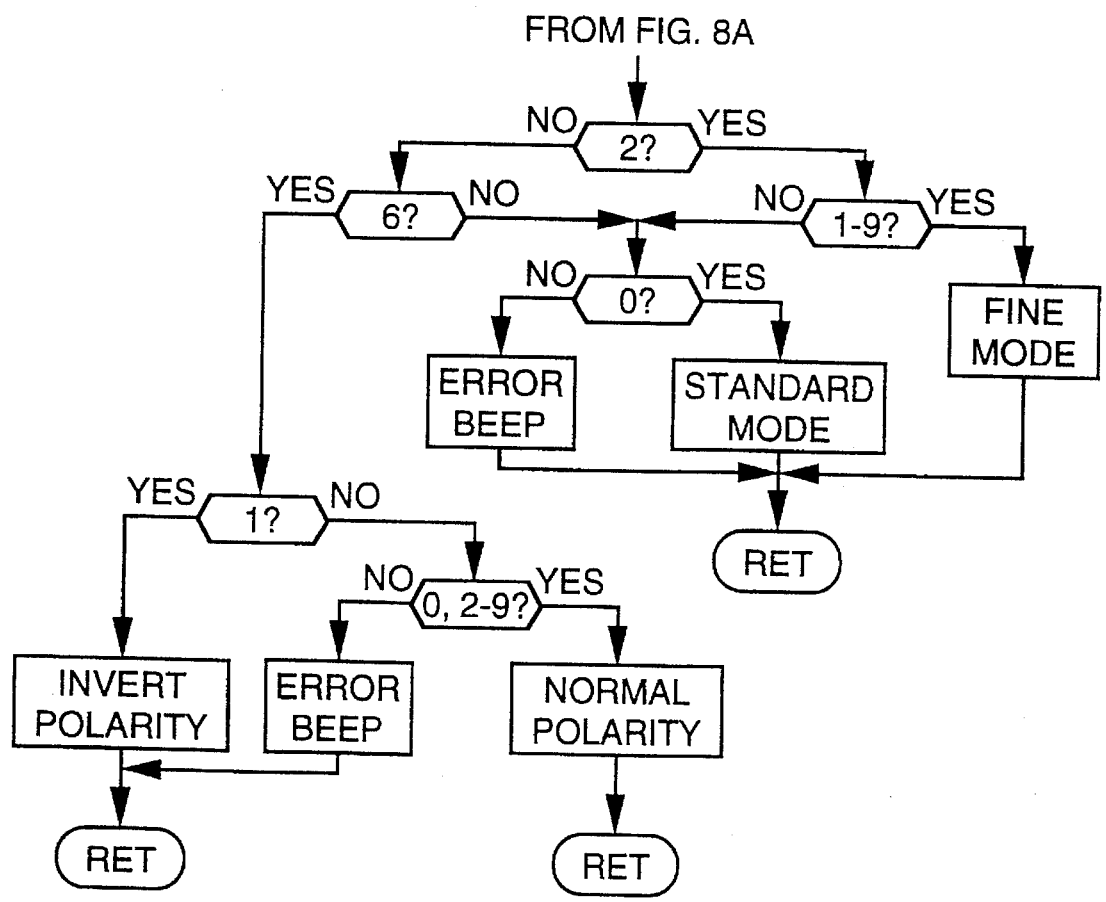

Referring now to FIGS. 6–8, there is shown (by way of software flowcharts) a preferred top-level operation of the control unit 10. It will be appreciated that the flowcharts of FIGS. 6–8 are sufficient to enable persons skilled in the art to write a specific program code (which is compatible with a particular microprocessor) to implement the concepts of the present invention. These flowcharts are intended to provide insight into the software operation of the present invention, rather than a direct correlation of the actual coded routines. For example, FIG. 6 includes blocks for receiving recorder data, console processing, and transmitting image data to a facsimile machine. In a preferred embodiment, these functions are actually performed in interrupt service routines.

FIG. 6 depicts the overall, endless looping flow of the software operation. Upon applying power to the control unit 10, the microprocessor 35 directs the software to begin execution at a predetermined address, where initialization and self-test routines are executed. This process checks and configures the hardware to ensure proper functionality for operation. The initialization routines include resetting software pointers to particular memory locations, and initializing the programmable hardware, such as the DUART 48, and the facsimile chip set 49, 50. To this end, values are written into the internal registers of the programmable chips, thereby supplying configuration and operating parameters.

Immediately following the initialization process, the microprocessor 35 executes various self-test routines. These routines include a self-test of the EPROM 36, RAM 37, DUART 48, and facsimile interface 30. The EPROM self-test routine includes testing the contents of the EPROM 36 with a checksum value, using a 16-bit cyclical redundancy code (CRC) algorithm. If the computed checksum value is the same as a particular checksum value stored in a predetermined EPROM location, then proper operation of the EPROM 36 is assumed.

A second self-test routine verifies proper working operations of the RAM 37. This is a 3-pass test, wherein the first pass involves having the microprocessor 35 write zeros to all RAM locations and then performing a read from all locations to ensure that a zero value was properly written to each. The second pass includes a "ones-write" test, whereby ones are written to all bit locations (i.e. the decimal value of 65,535 is written to all 16-bit memory locations). The microprocessor 35 then reads all of the memory locations to ensure that they were appropriately changed. The third pass is a similar write-read test that utilizes a pseudo-random write using a 32-bit CRC algorithm.

The DUART 48 is tested by placing both communication channels in a local loop-back mode. While in this mode, each channel is tested by transmitting four characters, which are "looped-back" and read into the receiving queue. The test verifies the timing of the transmission, the operation of the receiving queue, and the proper transmission of character data.

In the self-test routine for the facsimile interface 30, the facsimile micro-controller chip 49 is configured for transmission at 2400 bits per second and placed in a local loop-back mode. In this mode, a particular ASCII character value is programmed for transmission, then read back and checked separately.

It will, of course, be appreciated that, consistent with the design of the present invention, a variety of other self-tests could be employed with equal effectiveness. Accordingly, the specific self-test routines described above should be viewed as illustrative and not limiting to the operation of the present invention.

The progress of each of the self-test routines is displayed by a particular pattern or flashing of the LEDs on the control unit 10. In this way, diagnostic information is provided to the operator. In the event the control unit 10 is not functioning properly, inspection of the LEDs during the initialization provides valuable insight as to the possible source of error. More detailed diagnostics are supported through the use of the test computer 18.

Returning to the flowchart of FIG. 6, after the self-test routines are completed, the software enables the interrupts and the main program loop is entered. After enabling the interrupts, the software waits for either the receipt of data from the recorder unit 12 or the operator to take the telephone receiver off-hook, signalling the initiation of user operation. If neither event has occurred, the software determines whether a console interrupt has been generated. In the event that any of these conditions are satisfied, the appropriate action is taken. As previously mentioned, the flowchart of FIG. 6 is merely illustrative of the software operation. Indeed, it is preferred that the software code not make the specific tests for recorder data and console interrupt, since such events would automatically be triggered by virtue of the interrupt operation.

The console processing routine is provided for communication with a test computer 18 for developmental use, particularly during the manufacturing stage. As previously mentioned, it can also be used for further diagnostic purposes, in the event the control unit 10 has malfunctioned. This console processing routine accepts and executes particular commands entered from the test computer 18 for debugging purposes. Although it is not shown and described herein, it will be readily appreciated that the software supports the appropriate interpretation and execution of various commands entered from the test computer.

As is apparent from FIG. 6, the main program loop is repeatedly executed. Upon detection of a recorder transmission, a separate recorder data receive routine is entered. In this routine, described in further detail below, the control unit 10 receives and filters data transmitted from the recorder unit 12. After the data is completely received, another routine is executed to create a bit-image graphic of the ECG data. This imaging routine also includes image compression to create a graphic representation for transmission to a facsimile machine that conforms with the CCITT telephone system standards previously described.

After the compressed facsimile images have been generated, the control unit 10 is ready for transmission to a remote facsimile machine. The operator initiates transmission by depressing the "SEND" button provided on the control unit 10. Once the data is transmitted, the software loops back to a point where the user operation may be repeated.

FIG. 7 shows the software program flow for the recorder data receive routine. The first character received from the recorder unit 12 is used to establish the baud rate for the DUART 48. Permissible data rates include 19200 bits per second (the default rate), 9600 bits per second, 4800 bits per second, 2400 bits per second, and 1200 bits per second. In a preferred embodiment, the baud rate for the DUART 48 is established as follows: a special character "S" is sent from the recorder 12 to the control unit 10. Since the DUART 48 is, by default, receiving data at 19200 bits per second, this "S" character will only be received as an "S" if it is transmitted at 19200 bits per second as well. It will be appreciated, by virtue of the asynchronous serial data transmission, that this "S" character is received as a different character, for each different transmission rate. Accordingly, there are five unique receive characters that correlate to the transmitted "S" character, depending upon the data transmission rate. When the control unit 10 receives any of these five characters, it sets the baud rate of the DUART 48 accordingly.

After the baud rate for the DUART 48 has been established, the control unit responds to the recorder 12 by sending a "G" character. This signals the recorder to begin data transmission. The next character transmitted from the recorder 12 is the value 10FE (hexadecimal). The purpose of this character is merely to provide a check to ensure that the DUART 48 established the proper baud rate. Thus, if this character is not received, an error is presumed and the receive routine is restarted.

The third character (assuming proper baud rate coordination) received determines the type of communication message presently being transmitted from the recorder 12 to the control unit 10. More specifically, it determines whether the communication message is a data transfer or an acknowledgment request. If it is a data transfer message, then the data bytes of the message are sequentially read into the receive data queue and filtered. Upon completion of the data message, a checksum for that message is computed.

If, on the other hand, the communication message is an acknowledgment request, the checksum for the previous message is examined. If the checksum is zero, then the control unit 10 indicates to the recorder 12 that the previous message was successfully transferred. Otherwise, the control unit 10 signals to the recorder 12 and the user that an error was encountered during the last data message transmission and the data is deleted. This prompts the recorder 12, on command by the user, to retransmit the previous data message. Once the entire sampling of recorder data has been transferred to the control unit 10, the recorder receive routine is exited.

Referring next to FIG. 8, a top-level flowchart is shown of the tone programming routine. This figure should be considered in connection with Tables 1 and 2 below. In short, the tone programming routine allows an operator to call the control unit 10 from a remote telephone and thereby program certain user parameters into the unit's nonvolatile memory. Examples of these programmable parameters include the filter bandwidth, patient ID number, facsimile phone number, and various control codes (such as codes for turning off the call waiting feature during data transmission).

TABLE 1

| 1st Char | 2nd Char | OPTION NAME | Phone Digit | SETTING |
|---|---|---|---|---|
| 1 | 1 | Filter Bandwidth | 0 | None |
|  |  |  | 1 | 16 Hz low-pass |
|  |  |  | 2 | 18 Hz low-pass |
|  |  |  | 3 | 20 Hz low-pass |
|  |  |  | 4 | 22 Hz low-pass |
|  |  |  | 5 | 24 Hz low-pass |
|  |  |  | 6 | 28 Hz low-pass |
|  |  |  | 7 | 32 Hz low-pass |
|  |  |  | 8 | 36 Hz low-pass |
|  |  |  | 9 | 40 Hz low-pass |
| 1 | 2 | Print Mode | 1–9 | Fine Mode |
|  |  |  | 0 | Standard Mode |
| 1 | 3 | Patient I.D. Number | 0–9$^{ftn}$ | 12 digits including characters |
| 1 | 4 | Patient Phone Number | 0–9$^{ftn}$ | up to 32 digits including chars |
| 1 | 5 | Auto Dial Number | 0–9$^{ftn}$ | up to 32 digits including chars |
| 1 | 6 | Signal Polarity | 0, 2–9 | Normal Polarity |
|  |  |  | 1 | Invert Polarity |
| 2 |  | Reset |  | Resets default user parameter | ftn: Special characters are accessed by depressing the "#" key before pressing another key. These special characters are shown in Table 2.

The tone programming sequence is initiated and ended by pressing the "*" button on a touch-tone telephone. The particular sequence keyed between the "*" codes specifies the particular user parameters to be stored in the EEPROM 51. Table 1 lists permissible code sequences used in a preferred embodiment of the present invention. Of course, additional code sequences may be desirable for future versions of software. Any other sequence will generate an error signal, sounded on a piezo-electric buzzer, and the routine will exit without modifying any of the user parameters.

As an example, entering key sequence *2* causes default values of the user parameters to be stored in the EEPROM 51, which set the filter bandwidth to None (i.e., no filtering is performed), the print mode to Fine (i.e., advances facsimile printer by ½ increment), the signal polarity to normal, and set all remaining parameters to the null value. As another example, entering the sequence *115* sets the filter bandwidth at 24 hertz. As a still further example, entering the sequence *154337556* sets the phone number 433-7556 of the destination facsimile machine for automatic dialing by the control unit 10.

Special characters can be entered into the Patient ID field, the Patient Phone Number field or the Auto Dial Number field, by using the "#" key as a "shifting" function. That is, depressing the "#" key causes the next key to be interpreted as shifted. Table 2 shows a correlation of the normal telephone keys with their associated shifted interpretation, with the third column showing the action taken by the special characters. Thus, for example, entering the key sequence *15#04771234* programs the control unit 10 to wait for a dial tone, then autodial the number 477-1234. The sequence *13##* programs the control unit 10 to disable the call waiting feature during a facsimile transmission. The special characters may be cascaded such that, for example, the sequence *15606#1#04771234* programs the control unit to autodial 606, then pause and wait for a dial tone, then dial 477-1234.

TABLE 2

| Normal Key | Shifted "#" Key | ACTION TAKEN |
|---|---|---|
| 0 | @ | wait for dial tone |
| 1 | . | pause |
| 2 | ! | hook flash (on-hook/off-hook) |
| 3 | T | tone dialing |
| 4 | P | unused |
| 5 | W | wait period of time |
| 6 | - | used in patient I.D. |
| 7 | (space) | used in patient I.D. |
| 8 | / | used in patient I.D. |
| 9 | : | used in patient I.D. |
| * | * | used in patient I.D. |
| # | # | turns off call waiting (in some districts) |

Figure 9A:
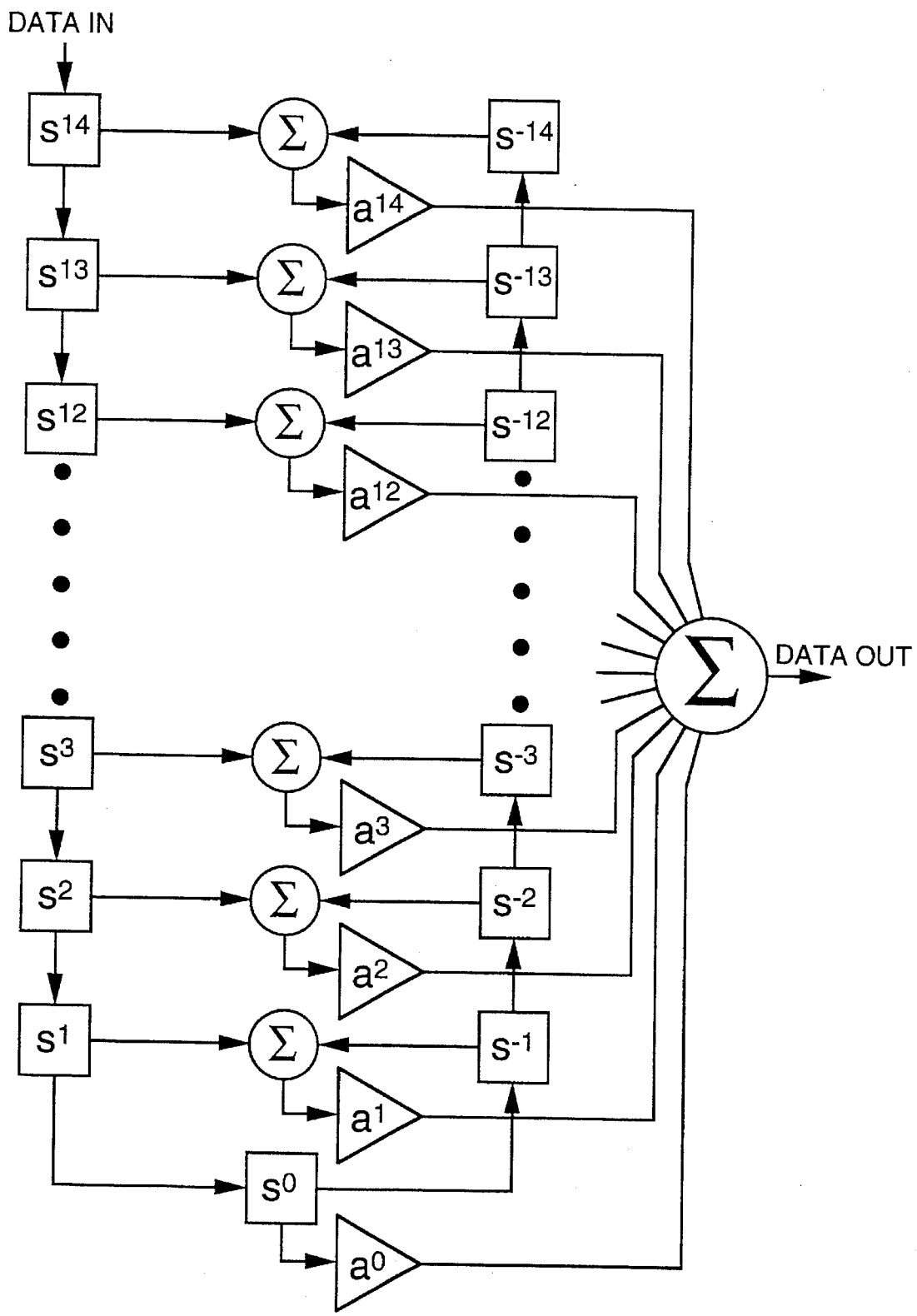
FIG. 9A is a block diagram showing the configuration of the finite impulse response digital filtering algorithm used in the present invention.

FIG. 9A illustrates the FIR filtering algorithm employed to provide the low-pass filtering operations of the present invention. In a preferred embodiment, a 29-stage symmetric filtering algorithm is utilized, whereby the number of multiply operations is virtually reduced to half. That is, the $s^n$ data value is summed with the $s^{-n}$ data value (where n is any integer between 1 and 14) before the multiply operation is performed. Thus, in this implementation fifteen, rather than twenty-nine, multiply operations are performed, decreasing the filter computation time.

Varying the individual gain values (i.e., the $a^n$ values) alters the filter characteristics. FIG. 9B shows a table of gain coefficient values for effectuating various low-pass filter bandwidths. In a preferred embodiment, the gain coefficients are chosen so as to make their sum equal to 256 (i.e., '100' hexadecimal) This enables scaling of the filter result to be achieved by a simple binary shift.

As previously mentioned, filtering is performed during the recorder data receiving routine. As the data characters are received, they are placed in a circular memory queue. The contents of this queue are used as input values for the FIR filter. The filtering begins when the fifteenth data character is received, so that the $s^0$ through $s^{14}$ filter blocks each have a data value from the present transmission. In a similar fashion, the last 14 points are filtered by repeating the last data value received, which is detected by a 30 millisecond interval where no further characters are received. The filter output is stored in a list for later access and use by the bit-image generation routine.

It will be appreciated that at all times during operation of the control unit 10, except during the tone programming and image transmission routines, the software control ensures that the line and phone relays 61, 62 are. de-energized so that the telephone is directly connected to the phone line. In this way, normal telephone operation is achieved without interference from the control unit 10 operation.

FIG. 10 depicts a facsimile printout illustrating a preferred graphical representation of transformed ECG data. The ECG data is plotted onto a graph, where three strips of graph data are positioned lengthwise on the printout. Each strip contains approximately 10 seconds of ECG data, for a total display of approximately 30 seconds per facsimile page. Information such as patient ID and filter bandwidth (not shown) may also be provided on the graphical output for identification by the physician. Alternatively, the patient ID and filter bandwidth may be provided on a separate facsimile cover sheet generated by the control unit 10.

The software of the present invention supports various modes of operation. The first, or "Storage," mode is used when the destination facsimile machine is operated by an attendant. In this mode, the user attaches the recorder 12 to the control unit 10 and dials the number of the physician's office. When directed to do so by the attendant, the user presses the recorder's transmit button 21, whereby the ECG data is transmitted to the control unit 10 at a high data rate (for example, in "burst" mode). After the control unit 10 has received the data and generated the compressed bit-image, the attendant at the physician's office starts the facsimile machine. Upon hearing the tones from the physician's facsimile machine, the patient presses the "SEND" button and the two devices begin their connect sequence.

In another, or "Auto-Dial," mode the user connects the recorder 12 and down-loads the ECG data to the control unit 10. The user then presses a "Transmit" button on the control unit 10, whereby the control unit 10 automatically dials the facsimile machine at the physician's office and transmits the images.

As can be seen from the foregoing detailed description, the present invention provides an improved apparatus and method for receiving electrocardiographic data and converting it to an appropriate format for transmission over standard telephone lines to a selected remote facsimile machine. The apparatus is preferably portable, and has modular connections which facilitate easy installation between a telephone and a phone line. The design of the apparatus is such that it can remain interconnected between the telephone and phone line without interfering with normal telephone operation, and such that it can be programmed by a person using a touch-tone telephone from a remote location.

We claim:

1. A remotely programmable apparatus for transmitting electrocardiographic (ECG) data to a remote facsimile machine, the apparatus comprising:

means for receiving ECG data from a recording unit;

filter means for removing undesired signals from the ECG data;

processing means coupled to the receiving means for converting the filtered ECG data into a graphical representation in the form of image data, the processing means being programmable by DTMF signals generated by a remote touch-tone telephone; and, converter means associated with the processing means for converting the image data generated by the processing means into a format prescribed by international communication standards and suitable for transmission over standard telephone lines to a facsimile machine, the converter means including a transmitter electrically coupled to a telephone line for communicating the converted image data to a selected remote facsimile machine and for receiving the DTMF signals from the remote touch-tone telephone, the converter means further including a DTMF decoder electrically connected to the transmitter for decoding the DTMF signals received from the transmitter and for forwarding the decoded DTMF signals to the processing means.

2. The apparatus of claim 1, wherein the digitized ECG data is received serially.

3. The apparatus of claim 1, wherein the compatible recording unit is portable and is physically detachable from the receiving means.

4. The apparatus of claim 1, further comprising isolation circuitry coupled between the receiving means and the processing means to electrically isolate the apparatus from the recording unit.

5. The apparatus of claim 2, further comprising a serial interface coupled to the receiving means for converting the digitized serial data received from the recording unit into a parallel format.

6. The apparatus of claim 1, wherein the processing means comprises:

a microprocessor for top-level control, non-volatile memory associated with the microprocessor for storing machine coded instructions for execution by the microprocessor, volatile memory coupled to the microprocessor for storing ECG data and other temporary data, and control logic electrically connected to the microprocessor, to the volatile memory and to the non-volatile memory for generating electrical control signals which synchronize the operations of the processing means.

7. The apparatus of claim 6, wherein the filter means is implemented by a filtering routine which is executed by the microprocessor.

8. The apparatus of claim 1, wherein the filtering routine utilizes a selected bandwidth which is selected by the microprocessor from among a set of possible bandwidths upon receipt of a predetermined DTMF code sequence from the remote touch-tone telephone.

9. The apparatus of claim 1, wherein the converter means is implemented by machine coded software instructions executed by the microprocessor to convert the image data into a format suitable for transmission over standard telephone lines and by a facsimile interface coupled between the microprocessor and the telephone line, the transmitter and the DTMF decoder being associated with the facsimile interface.

10. The apparatus of claim 1, said apparatus being adapted for programmable control by a remote touch-tone telephone.

11. The apparatus of claim 1, wherein the processing means adjusts the bandwidth of the filter means in accordance with the DTMF signals received from the remote touch-tone telephone.

12. The apparatus of claim 1, wherein the DTMF signals received from the remote touch-tone telephone are representative of a telephone number corresponding to the selected remote facsimile machine and the processing means employs the telephone number to automatically dial the selected facsimile machine.

13. An apparatus for transmitting electrocardiographic (ECG) data to a remote facsimile machine, the apparatus comprising:

means for receiving ECG data from a recording unit;

filter means for removing undesired signals from the ECG data;

processing means coupled to the receiving means for converting the filtered ECG data into a graphical representation in the form of image data;

converter means associated with the processing means for converting the image data generated by the processing means into a format prescribed by international communication standards and suitable for transmission over standard telephone lines to a facsimile machine, the converter means including a transmitter electrically coupled to a telephone line for communicating the converted image data to a selected remote facsimile machine; and, a switching network electrically connected to a local telephone, to the phone line, to the converter means and to the processing means, the switching network being configured to connect the local telephone to the phone line in response to a first control signal from the processing means to thereby render the apparatus transparent to the local telephone and to connect the converter means to the phone line in response to a second control signal from the processing means.

14. The apparatus according to claim 13, wherein the switching network is configured to disconnect the converter means from the phone line in response to the first control signal from the processing means and to disconnect the local telephone from the phone line in response to the second control signal from the processing means.

15. The apparatus according to claim 13, further comprising a DTMF decoder to receive and interpret DTMF signals to provide programmable control of the processing means from a remote touch-tone telephone.

16. The apparatus according to claim 15, wherein the filter means is configured to pass signals having a frequency falling within a bandwidth defined by a range of acceptable signal frequencies.

17. The apparatus according to claim 16, wherein the processing means controllably varies the filter bandwidth in response to the DTMF signals received from the remote touch-tone telephone.

18. The apparatus according to claim 15, wherein the processing means incorporates a patient identification number into the facsimile image.

19. The apparatus according to claim 18, wherein the processing means controllably varies the patient identification number in response to the DTMF signals received from the remote touch-tone telephone.

* * * * *

UNITED STATES PATENT AND TRADEMARK OFFICE
CERTIFICATE OF CORRECTION

PATENT NO. : 5,581,369
DATED : December 3, 1996
INVENTOR(S) : Righter et al.

It is certified that error appears in the above-identified patent and that said Letters Patent is hereby corrected as shown below:

In Column 12, line 64: after "are" delete "."

Claim 2: In Column 14, line 4, "claim 1" should read --claim 10--.
Claim 8: In Column 14, line 31, "claim 1" should read --claim 7--.
Claim 9: In Column 14, line 36, "claim 1" should read --claim 6--.
Claim 10 should read --The apparatus of claim 1, wherein the ECG data received from the recording unit is in digitized form.--.

Signed and Sealed this

Twenty-fifth Day of March, 1997

Attest:

BRUCE LEHMAN

Attesting Officer  Commissioner of Patents and Trademarks